US012667407B2

(12) United States Patent
Zhong et al.

(10) Patent No.: US 12,667,407 B2
(45) Date of Patent: Jun. 30, 2026

(54) PULSE CONTROL METHOD AND APPARATUS, ABLATION DEVICE AND SYSTEM, AND STORAGE MEDIUM

(71) Applicant: Hangzhou Wknife Medical Technology Co., Ltd, Hangzhou (CN)

(72) Inventors: Xinghua Zhong, Hangzhou (CN); Long Wang, Hangzhou (CN); Ke Yang, Hangzhou (CN)

(73) Assignee: Hangzhou Wknife Medical Technology Co., Ltd, Hangzhou (CN)

( * ) Notice: Subject to any disclaimer, the term of this patent is extended or adjusted under 35 U.S.C. 154(b) by 276 days.

(21) Appl. No.: 18/286,953

(22) PCT Filed: Apr. 12, 2022

(86) PCT No.: PCT/CN2022/086396
§ 371 (c)(1),
(2) Date: Oct. 13, 2023

(87) PCT Pub. No.: WO2022/218312
PCT Pub. Date: Oct. 20, 2022

(65) Prior Publication Data
US 2024/0189014 A1      Jun. 13, 2024

(30) Foreign Application Priority Data

Apr. 15, 2021      (CN) .......................... 202110406282.5

(51) Int. Cl.
*A61B 18/12*          (2006.01)
*A61B 18/14*          (2006.01)
(Continued)

(52) U.S. Cl.
CPC ...... *A61B 18/1206* (2013.01); *A61B 18/1477* (2013.01); *A61N 1/327* (2013.01);
(Continued)

(58) Field of Classification Search
CPC ........... A61B 2018/00613; A61B 2018/00672; A61B 2018/00678; A61B 2017/00159; A61N 1/327
See application file for complete search history.

(56) References Cited

U.S. PATENT DOCUMENTS

2008/0132885 A1      6/2008 Rubinsky et al.
2015/0289923 A1      10/2015 Davalos et al.
(Continued)

FOREIGN PATENT DOCUMENTS

CN          107681916 A  *  2/2018  ......... A61B 18/1492
CN          110693606 A      1/2020
(Continued)

OTHER PUBLICATIONS

International Search Report for PCT/CN2022/086396 mailed Jul. 8, 2022. 4 pgs.
(Continued)

*Primary Examiner* — Jaymi E Della
(74) *Attorney, Agent, or Firm* — Ladas & Parry, LLP

(57)          ABSTRACT

A pulse control method and apparatus, an ablation device and system, and a storage medium. The pulse control method comprises: controlling a pulse generator to output a nanosecond pulse sequence and a millisecond pulse sequence, the amplitude of the nanosecond pulse sequence being greater than a preset first threshold voltage, and the amplitude of the millisecond pulse sequence being less than a preset second threshold voltage. The nanosecond pulse sequence having the amplitude greater than the threshold voltage cooperates with the millisecond pulse sequence having the amplitude less than the threshold voltage, such that the effective ablation range can be enlarged, the ablation (Continued)

is more thorough, the muscle contraction amplitude can be effectively reduced, or the muscle contraction probability is reduced.

17 Claims, 6 Drawing Sheets

(51) Int. Cl.
   *A61N 1/32*          (2006.01)
   *A61B 17/00*         (2006.01)
   *A61B 18/00*         (2006.01)

(52) U.S. Cl.
   CPC ............... *A61B 2017/00159* (2013.01); *A61B 2018/00577* (2013.01); *A61B 2018/00613* (2013.01); *A61B 2018/00672* (2013.01); *A61B 2018/00678* (2013.01); *A61B 2018/00761* (2013.01); *A61B 2018/1425* (2013.01)

(56)                References Cited

U.S. PATENT DOCUMENTS

2016/0100879 A1* 4/2016 Long ................. A61B 18/1233
                                                              606/35

2016/0184003 A1* 6/2016 Srimathveeravalli .......................
                                                           A61B 18/1233
                                                                606/39
2019/0357960 A1* 11/2019 Rubinsky .............. A61M 1/916
2020/0289827 A1* 9/2020 Forsyth ................. A61B 18/12
2022/0096151 A1* 3/2022 Shuros .............. A61B 18/1233

FOREIGN PATENT DOCUMENTS

CN       111437513  A      7/2020
CN       111529050  A  *  8/2020  ............ A61B 18/12
CN       112540221  A      3/2021
CN       113100918  A      7/2021
WO   WO-2023049954 A1 *  4/2023  ............ A61M 25/10

OTHER PUBLICATIONS

Second Office Action for Chinese Application No. 202110406282.5 issued Aug. 3, 2022. 8 pgs.
Rejection Decision for Chinese Application No. 202110406282.5 issued Jan. 28, 2023. 6 pgs.
First Office Action for Chinese Application No. 202110406282.5 issued Apr. 2, 2022. 9 pgs.

* cited by examiner

PULSE CONTROL METHOD AND APPARATUS, ABLATION DEVICE AND SYSTEM, AND STORAGE MEDIUM

CROSS-REFERENCE TO RELATED APPLICATIONS

This application is a National Stage of International Application No. PCT/CN2022/086396, filed on Apr. 12, 2022, which claims priority to Chinese Patent Application No. 202110406282.5, filed on Apr. 15, 2021.

TECHNICAL FIELD

The present application relates to the technical field of medical equipment, and in particular, the present application relates to a pulse control method and a pulse control apparatus, an ablation device and an ablation system, and a storage medium.

BACKGROUND

Electroablation mainly uses an electroporation phenomenon, in which electric-field pulses are transmitted to lesion cells, such that ions inside and outside the cells move and are gathered on both sides of the outer cell membranes, causing a drastic change in a transmembrane potential and the occurrence of electroporation in the outer cell membrane, so as to break equilibrium between the inside and outside of the cell, and thus achieving an ablation purpose.

However, an existing electroablation solution usually has defects such as having a small ablation range and a poor ablation effect, being prone to incurring muscle contractions such that a patient has poor experience, and needing to be used in combination with an anesthetic and thus having a high treatment cost.

SUMMARY

For the disadvantages of an existing method, the present application provides a pulse control method and a pulse control apparatus, an ablation device and an ablation system, and a storage medium, which are used for solving at least one aspect of the above-mentioned technical problems in the prior art at least to a certain extent.

In a first aspect, an embodiment of the present application provides a pulse control method, including:

controlling a pulse generator to output a nanosecond pulse sequence, and controlling the pulse generator to output a millisecond pulse sequence.

wherein an amplitude of the nanosecond pulse sequence is greater than a preset first threshold voltage, and an amplitude of the millisecond pulse sequence is less than a preset second threshold voltage.

In a second aspect, an embodiment of the present application provides a pulse control apparatus, including:

an electric pulse control module configured to control a pulse generator to output a nanosecond pulse sequence and control the pulse generator to output a millisecond pulse sequence; and control an amplitude of the nanosecond pulse sequence to be greater than a preset first threshold voltage and control an amplitude of the millisecond pulse sequence to be less than a preset second threshold voltage.

In a third aspect, an embodiment of the present application provides an ablation device, including:

an electrode needle configured to contact a target object and output an electric pulse to the target object;

a pulse generator electrically connected to the electrode needle and configured to generate an electric pulse and conduct the electric pulse to the electrode needle; and a controller communicatively connected with the pulse generator and configured to perform the pulse control method according to the embodiment of the first aspect of the present disclosure.

In a fourth aspect, an embodiment of the present application provides an ablation system, including the ablation device as provided in the third aspect and an upper computer.

The upper computer is communicatively connected with the controller in the ablation device.

In a fifth aspect, an embodiment of the present application provides a computer-readable non-volatile storage medium having a computer program stored thereon, the computer program, when executed by a processor, implementing the pulse control method according to the embodiment of the first aspect.

The beneficial technical effects brought about by the technical solutions provided in the embodiments of the present application are as follows. By means of a nanosecond pulse sequence having the amplitude greater than a threshold voltage cooperating with a millisecond pulse sequence having the amplitude less than a threshold voltage, for example, by means of a cooperative action of a high-voltage nanosecond pulse sequence and a low-voltage millisecond pulse sequence, an effective ablation range can be enlarged, and the ablation can be more thorough; the muscle contraction amplitude can be effectively reduced or the muscle contraction probability can be reduced, thereby improving the treatment experience of a patient; and the use of anesthetics can be reduced, thereby effectively reducing treatment costs and reducing side effects.

Specifically, the high-voltage nanosecond pulse sequence can cause irreversible electroporation to occur in cells close to the electrode needle such that the cells enter an apoptosis process, and cause reversible electroporation to occur in cells relatively far from the electrode needle. The low-voltage millisecond pulse sequence can conduct electrolysis of the cells relatively far from the electrode needle in which reversible electroporation occurs (water and an electrolyte are present in the cells, and under a certain electrolysis condition, the electrolyte may be bound with hydroxide ions generated by water electrolysis, so as to reduce the concentration of the electrolyte, such that osmotic pressure equilibrium, acid-base equilibrium, water equilibrium, etc. of the cells may be broken, thereby destroying cell activity), and thus the cells relatively far from the electrode needle may also enter the apoptosis process. Therefore, compared with the existing electroablation solution, a larger ablation treatment range and more thorough ablation are achieved by means of the technical solution provided in the embodiments of the present application.

Moreover, the high-voltage nanosecond pulse sequence facilitates reduction in muscle stress contractions due to parameter characteristics thereof, and the low-voltage millisecond pulse sequence also does not cause any muscle stress contraction due to a relatively low voltage used thereby. Therefore, by means of the technical solution provided in the embodiments of the present application, muscle contractions of a patient during treatment can be greatly relieved, thereby improving the treatment experience of the patient.

Additional aspects and advantages of the present application will be set forth in part in the following description, which will become apparent from the following description, or may be learned by practice of the present application.

BRIEF DESCRIPTION OF THE DRAWINGS

The above and/or additional aspects and advantages of the present application will become apparent and easily comprehensible from the following description of embodiments in below in conjunction with drawings.

Figure 1:
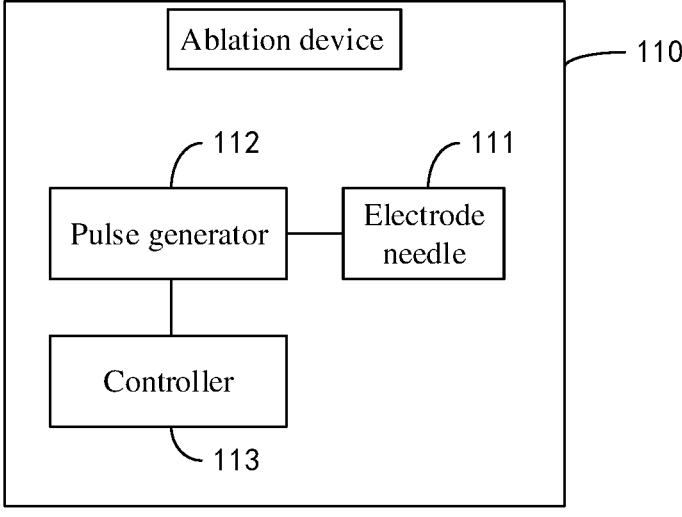
FIG. 1 is a schematic diagram of a framework of the structure of an ablation device provided in an embodiment of the present application.

100—Ablation system;

110—Ablation device; 111—Electrode needle; 112—Pulse generator; 112*a*—First sub-generator;

112*b*—Second sub-generator; 113—Controller;

120—Upper computer;

1—Nanosecond pulse; 2—Millisecond pulse;

10—Nanosecond pulse sub-sequence; 20—Millisecond pulse sub-sequence.

DETAILED DESCRIPTION

The present application will be described in detail below. Examples of the embodiments of the present application are shown in the drawings, and throughout the drawings, the same or similar reference signs refer to the same or similar components or components having the same or similar functions. In addition, the detailed description of known techniques will be omitted if unnecessary to the shown features of the present application. The embodiments described below with reference to the drawings are exemplary and are merely used to be illustrative of the present application, but should not be construed as limiting the present application.

It should be understood by the skilled in the art that, unless otherwise defined, all terms (including technical and scientific terms) used herein have the same meaning as commonly understood by those of ordinary skills in the art. It should also be understood that terms, such as those defined in commonly used dictionaries, should be construed as having meanings that are consistent with their meanings in the context of the prior art, and will not be construed in an idealized or overly formal sense unless specifically defined as here.

It should be understood by the skilled in the art that, as used herein, the singular form "a", "an" or "the" may include plural forms as well, unless otherwise stated. It should be further understood that the term "include" used in the specification of the present application specifies the presence of the features, integers, steps, operations, elements and/or components, but does not exclude the presence or addition of one or more of other features, integers, steps, operations, elements, components and/or their combinations. It should be understood that, when an element is referred to be "connected to" or "coupled to" another element, this element may be directly connected to or coupled to the another element, or this element may be connected to the another element through an intermediate element. In addition, "connection" or "coupling" used herein may include wireless connection or wireless coupling. The term "and/or" used herein indicates all or any units and all combinations of one or more items listed in association.

First, a few terms involved in the present application will be introduced and explained.

Threshold voltage: a threshold voltage refers to a critical voltage value for demarcating adjacent voltage intervals, for example, a voltage value for demarcating a high-voltage interval and a low-voltage interval, for example, 144 volts (V) to 1000 V.

The inventors of the present application have found by studies that, in an existing solution of treating tumors using electric pulses, treatment can be performed using a microsecond pulse or a nanosecond pulse, separately, in which irreversible electroporation may occur in cells close to an electrode needle such that the cells enter an apoptosis process, whereas reversible electroporation occurs to cells away from the electrode needle. The cells may survive after reversible electroporation, and thus an expected ablation effect cannot be achieved. Therefore, the existing electroablation solution has the defects of having a relatively small ablation range and being incapable of achieving thorough ablation.

It is necessary to increase a pulse voltage to achieve an expected treatment effect. However, a high-voltage pulse may cause a patient to have muscle stress contractions during treatment, which seriously affects the treatment experience of the patient, and results in that treatment often needs to be performed with an anesthetic to relieve muscle contractions. The use of the anesthetic may increase the treatment cost, and also bring about certain side effects to the patient.

The pulse control method and the pulse control apparatus, the ablation device and the ablation system and the storage medium provided by the present application aim to solve the above technical problems in the prior art.

The technical solution of the present application, and how the technical solution of the present application solves the above technical problems will be described below in detail with particular embodiments.

An embodiment of the present application provides an ablation device 110. FIG. 1 shows a schematic structural diagram of the ablation device, which includes but is not limited to an electrode needle 111, a pulse generator 112 and a controller 113.

The electrode needle 111 is configured to contact a target object and output an electric pulse to the target object. For example, the electrode needle may be configured to extend into a target biological tissue and output an electric pulse to the target biological tissue.

The pulse generator 112 is electrically connected to the electrode needle 111 and is configured to generate an electric pulse and conduct the electric pulse to the electrode needle.

The controller 113 is communicatively connected with the pulse generator 112 and configured to perform any pulse control method provided in the embodiments of the present application. The pulse control method will be described below in detail, and will not be repeated here.

In the present embodiment, the controller 113 may be configured to control the pulse generator 112 to generate a nanosecond pulse sequence and a millisecond pulse sequence and output the nanosecond pulse sequence and the millisecond pulse sequence to the electrode needle 111. The electrode needle 111 may be configured to apply the nanosecond pulse sequence and the millisecond pulse sequence to the target biological tissue.

The nanosecond pulse sequence having an amplitude greater than a threshold voltage may be a high-voltage nanosecond pulse sequence, and the millisecond pulse sequence having an amplitude less than a threshold value may be a low-voltage millisecond pulse sequence.

The high-voltage nanosecond pulse sequence can cause irreversible electroporation to occur in cells close to the electrode needle 111 such that the cells enter an apoptosis process, and cause reversible electroporation to occur in cells relatively far from the electrode needle 111. The low-voltage millisecond pulse sequence can conduct electrolysis of the cells relatively far from the electrode needle 111 in which reversible electroporation occurs (water and an electrolyte are present in the cells, and under a certain electrolysis condition, the electrolyte may be bound with hydroxide ions generated by water electrolysis, so as to reduce the concentration of the electrolyte, such that osmotic pressure equilibrium, acid-base equilibrium, water equilibrium, etc. of the cells may be broken, thereby destroying cell activity), and thus the cells relatively far from the electrode needle 111 may also enter the apoptosis process. Therefore, compared with the existing electroablation solution, a larger ablation treatment range and more thorough ablation can be achieved by means of the ablation device 110 provided in the embodiments of the present application.

Moreover, the high-voltage nanosecond pulse sequence facilitates reduction in muscle stress contractions due to parameter characteristics thereof, and the low-voltage millisecond pulse sequence also does not cause any muscle stress contraction due to a relatively low voltage used thereby. Therefore, by means of the ablation device 110 provided in the embodiments of the present application, during ablation, the muscle contraction amplitude of a patient or the muscle contraction probability of the patient can be effectively reduced, or muscle contractions can even be avoided, thereby improving the treatment experience of the patient; and the use of anesthetics can be reduced or even not needed, thereby effectively reducing the treatment costs and reducing side effects.

Figure 2:
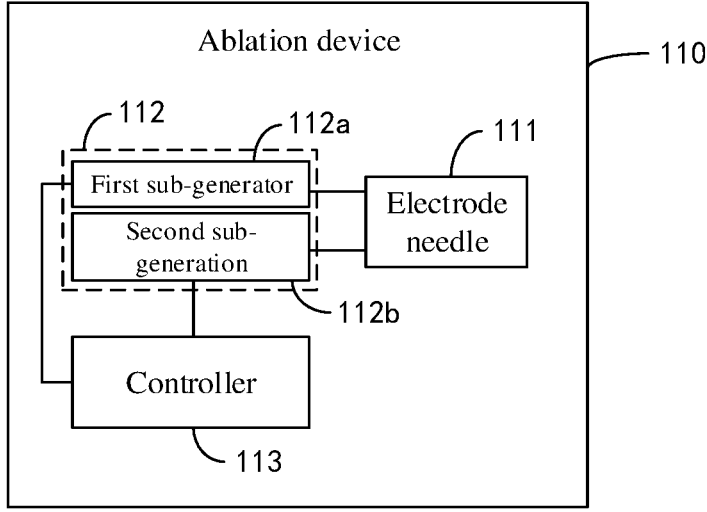
FIG. 2 is a schematic diagram of a framework of the structure of another ablation device provided in an embodiment of the present application.

In some possible exemplary embodiments, as shown in FIG. 2, the pulse generator 112 includes, but not limited to: a first sub-generator 112a and a second sub-generator 112b.

The first sub-generator 112a is electrically connected to the electrode needle 111, communicatively connected with the controller 113 and configured to generate a nanosecond pulse sequence.

The second sub-generator 112b is electrically connected to the electrode needle 111, communicatively connected with the controller 113 and configured to generate a millisecond pulse sequence.

In the present embodiment, the structure of the pulse generator 112 includes two pulse sub-generators, so as to realize separate generation of a nanosecond pulse sequence and a millisecond pulse sequence, thereby facilitating circuit designs of the pulse sub-generators. For example, corresponding pulse parameters are realized by means of a physical structure of a circuit. For example, a circuit structure of the first sub-generator 112a is configured to be capable of generating a required nanosecond pulse sequence, and a circuit structure of the second sub-generator 112b is configured to be capable of generating a required millisecond pulse sequence.

Optionally, the first sub-generator 112a and the second sub-generator 112b may be two pulse generation chips that are integrated on the same circuit board.

Optionally, the first sub-generator 112a and the second sub-generator 112b may be separate pulse generation units that are respectively located on different circuit boards.

In some possible exemplary embodiments, the ablation device 110 may also include, but not limited to: a memory. The controller 113 is electrically connected to the memory by means of, for example, a bus. Optionally, the controller 113 may be a central processing unit (CPU), a general-purpose processor, a digital signal processor (DSP), an application specific integrated circuit (ASIC), a field-programmable gate array (FPGA) or other programmable logic devices, transistor logic devices, hardware components, or any combination thereof. The controller can implement or execute various exemplary logic blocks, modules and circuits described in conjunction with the disclosure of the present application. The controller 113 may also be a combination for realizing computing functions, such as a combination including one or more microprocessors, a combination of a DSP and a microprocessor, and so on.

Optionally, the bus may include, but not limited to a path through which information is transferred between the above components. The bus may be a peripheral component interconnect (PCI) bus or an extended industry standard architecture (EISA) bus and so on. The bus may include an address bus, a data bus, a control bus, and so on.

Optionally, the memory may be a read-only memory (ROM) or other types of static storage devices that may store static information and instructions, a random access memory (RAM) or other types of dynamic storage devices that may store information and instructions, it may also be an electrically erasable programmable read only memory (EE-PROM), a compact disc read-only memory (CD-ROM) or other optical disk storages, optical disk storages (including a compressed compact disc, a laser disc, a compact disc, a digital versatile disc, a blu-ray disc, etc.), a magnetic disk storage medium, or other magnetic storage devices, or any other medium capable of carrying or storing expected program codes of an instruction or data structure form and capable of being accessed by a computer, without limitation therein.

In some possible exemplary embodiments, the ablation device 110 may also include, but not limited to a monitoring unit. The monitoring unit may be configured to monitor a current and/or a voltage parameter of the electrode needle 111, and the controller 113 determines an operation state of the electrode needle 111 according to the current and/or voltage parameter of the electrode needle 111 obtained by the monitoring unit. For example, when the present current and/or voltage parameter of the electrode needle 111 obtained by the monitoring unit corresponds to a current and/or voltage of the electrode needle 111 with no load (no connected to any load), then it is considered that the electrode needle 111 has completed the outputting of an electric pulse sequence.

In some possible exemplary embodiments, the ablation device 110 may also include, but not limited to a transceiver. The transceiver may be used to receive and send signals. The transceiver may allow wireless or wired communication between the controller 113 of the ablation device 110 and another device for data exchange. For example, when the controller 113 receives, by means of the transceiver, an ablation stop instruction or a needle withdraw instruction inputted by a user, the controller 113 is triggered to control the pulse generator 112 to start outputting an electric pulse sequence, or control the pulse generator 112 to stop outputting the electric pulse sequence. It should be noted that the number of transceivers in actual application is not limited to one.

In some possible exemplary embodiments, the ablation device 110 may also include, but not limited to an input unit. The input unit may be configured to receive inputted information of digits, characters, images and/or speech, or generate a key signal input related to user settings and function control of the controller 113. The input unit may include, but not limited to one or more of a touch screen, a physical keyboard, a function key (e.g., a volume control key and a power key), a trackball, a mouse, a joy stick, a camera device, a pickup, etc.

In some possible exemplary embodiments, the ablation device 110 may also include, but not limited to an output unit. The output unit may be configured to output or present information processed by means of the controller 113. The output unit may include, but not limited to one or more of a display device, a loudspeaker, a vibration device, etc.

It should be understood by the skilled in the art that the controller 113 of the ablation device 110 provided in the embodiments of the present application may be specifically designed and manufactured for a required purpose, or may also include, but not limited to known devices in a general-purpose computer. These devices have computer programs stored therein, and these computer programs are selectively activated or reconstructed. Such computer programs may be stored in a device (e.g., a computer)-readable medium or stored in any types of mediums that are suitable for storing electronic instructions and are respectively coupled to a bus.

On the basis of the same inventive concept, an embodiment of the present application provides a pulse control method. The method includes, but not limited to:

controlling a pulse generator to output a nanosecond pulse sequence and controlling the pulse generator to output a millisecond pulse sequence. Pulses outputted by the pulse generator may be used for outputting a nanosecond pulse sequence and a millisecond pulse sequence to a target biological tissue. An amplitude of the nanosecond pulse sequence is greater than a preset first threshold voltage, and an amplitude of the millisecond pulse sequence is less than a preset second threshold voltage.

Optionally, the controller 113 in the ablation device 110 provided in the foregoing embodiments controls the pulse generator 112 to generate a nanosecond pulse sequence and a millisecond pulse sequence and output the nanosecond pulse sequence and the millisecond pulse sequence to the electrode needle 111, and causes the electrode needle 111 to output the nanosecond pulse sequence and the millisecond pulse sequence to a target biological tissue.

In the present embodiment, the nanosecond pulse sequence having an amplitude greater than the preset first threshold voltage may be a high-voltage nanosecond pulse sequence, and the millisecond pulse sequence having an amplitude less than the preset second threshold voltage may be a low-voltage millisecond pulse sequence.

In some embodiments, a pulse amplitude voltage of the nanosecond pulse sequence may be set between 5 kV and 100 kV, that is, the preset first threshold voltage may be between 5 kV and 100 kV. A pulse amplitude voltage of the millisecond pulse sequence may be set between 5 kV and 100 kV, that is, the preset first threshold voltage may be between 5 kV and 100 kV.

In some embodiments, outputting the nanosecond pulse sequence to the target biological tissue may induce occurrence of irreversible electroporation in cells in a first region (typically corresponding to a region relatively closer to the electrode needle) of the target biological tissue, and induce occurrence of reversible electroporation in cells in a second region (typically corresponding to a region relatively farther away from the electrode needle) of the target biological tissue.

Since electropores exist in only a certain time window when reversible electroporation occurs in a cell membrane, for achieving a treatment effect in an existence duration of reversible electropores, in some embodiments, the millisecond pulse sequence is outputted to the target biological tissue in an existence duration of at least some of the reversible electropores of the cells in the second region, so as to induce start of cell apoptosis of cells in the second region.

In this way, using the electroporation phenomenon of cell membranes in the existence duration of the reversible electropores, an electric field induced by millisecond pulses more easily penetrates the cell membranes to act on the interiors of the cells of the target biological tissue, such that effects caused by the electric field, such as cell electrolysis, are realized more easily, so as to induce cell apoptosis.

It should be understood that, for the first region in which irreversible electropores exist, due to the existence of electropores of the cell membranes, it is obvious that the electric field induced by the millisecond pulses also more easily acts on the target biological tissue, such that electric field effects such as cell electrolysis are realized more easily, so as to induce cell apoptosis in the first region along with the action of the irreversible electropores themselves on the cells, under the joint action of the nanosecond and millisecond pulses.

Cell apoptosis is different from cell necrosis, where apoptosis can promote cell death using an immunologic function of a human body, and apoptotic cells may be identified as normal dead cells by the human body and removed by means of cytophagocytosis, which facilitates regeneration and repair of a normal tissue, and thus better facilitates recovery of a physiological function of an ablation region. Therefore, according to the method of the present disclosure, during treatment of cancers, etc., a better treatment effect can be achieved than ablation with only nanosecond pulses, or ablation with only millisecond pulses.

It should be noted that, in the present disclosure, the millisecond pulse indicates a pulse having a millisecond-level pulse width so as to be distinguished from a pulse having a nanosecond-level pulse width, and it is not limited to a pulse having pulse width of necessarily several milliseconds. For example, in some embodiments, the pulse width of the millisecond pulse may be between 1 millisecond and 1000 milliseconds.

It should be understood that the duration of reversible electropores of the target biological tissue may be different depending on different forms of the target biological tissue, different nanosecond pulse excitation and different distances from the electrode needle. The skilled in the art can select a corresponding pulse generation parameter according to the specific treatment scenario under the teaching of the present disclosure, and these selected parameters also fall within the scope of protection of the present application.

In some embodiments of the present disclosure, the nanosecond pulse sequence and the millisecond pulse sequence are alternately outputted to the target biological tissue, so that a set interval exists between an ending time of at least one nanosecond pulse and a starting time of a following adjacent millisecond pulse, and the set interval is not longer than 1 second.

In some embodiments, a time interval from an end of a nanosecond pulse to a start of a millisecond pulse may be negative, that is, the millisecond pulse may occur at the same time when the nanosecond pulse occurs, such that the nanosecond pulse and the millisecond pulse act on the target biological tissue at the same time.

In the pulse control method provided in the present embodiment, a nanosecond pulse sequence having an amplitude greater than a preset first threshold voltage cooperates with a millisecond pulse sequence having an amplitude less than the present second threshold voltage, such that the effective ablation range can be enlarged, and the ablation can be more thorough; the muscle contraction amplitude or the muscle contraction probability can be effectively reduced, and muscle contractions can even be avoided, thereby improving the treatment experience of a patient; and the use of anesthetics can be reduced or even not needed, thereby effectively reducing treatment costs and reducing side effects.

Specifically, the high-voltage nanosecond pulse sequence can cause irreversible electroporation to occur in cells close to the electrode needle 111 such that the cells enter an apoptosis process, and cause reversible electroporation to occur in cells relatively far from the electrode needle 111. The low-voltage millisecond pulse sequence can conduct electrolysis of the cells relatively far from the electrode needle 111 in which reversible electroporation occurs (water and an electrolyte are present in the cells, and under a certain electrolysis condition, the electrolyte may be bound with hydroxide ions generated by water electrolysis, so as to reduce the concentration of the electrolyte, such that osmotic pressure equilibrium, acid-base equilibrium, water equilibrium, etc. of the cells may be broken, thereby destroying cell activity), and thus the cells relatively far from the electrode needle 111 may also enter the apoptosis process. Therefore, compared with the existing electroablation solution, a larger ablation treatment range and more thorough ablation are achieved by means of the technical solution provided in the embodiments of the present application.

Moreover, the high-voltage nanosecond pulse sequence facilitates reduction in muscle stress contractions due to parameter characteristics thereof, and the low-voltage millisecond pulse sequence also does not cause any muscle stress contraction due to a relatively low voltage used thereby. Therefore, by means of the technical solution provided in the embodiments of the present application, muscle contractions of a patient during treatment can be greatly relieved, and even no muscle contraction occurs, thereby improving the treatment experience of the patient.

On the basis of the same inventive concept, an embodiment of the present application provides another pulse control method. The method includes, but not limited to:

alternatively outputting a nanosecond pulse sequence and a millisecond pulse sequence to a target biological tissue. An amplitude of the nanosecond pulse sequence is greater than a preset first threshold voltage, and an amplitude of the millisecond pulse sequence is less than a preset second threshold voltage.

Optionally, the controller 113 in the ablation device 110 provided in the foregoing embodiments controls the pulse generator 112 to alternately generate a nanosecond pulse sequence and a millisecond pulse sequence and output same to the electrode needle 111, and cause the electrode needle 111 to alternately output the nanosecond pulse sequence and the millisecond pulse sequence to the target biological tissue.

In the another pulse control method provided in the present embodiment, the nanosecond pulse sequence having the amplitude greater than the threshold voltage also cooperates with the millisecond pulse sequence having the amplitude less than the threshold voltage, such that the effective ablation range can be enlarged, and the ablation can be more thorough; the muscle contraction amplitude or the muscle contraction probability can be effectively reduced, or muscle contractions can even be avoided, thereby improving the treatment experience of a patient; and the use of anesthetics can be reduced or even not needed, thereby effectively reducing treatment costs and reducing side effects.

In the present embodiment, the nanosecond pulse sequence and the millisecond pulse sequence are alternately outputted to the target biological tissue, so as to facilitate controlling the length of the high-voltage nanosecond pulse sequence, that is, controlling an action duration of each high-voltage nanosecond pulse sequence on the target biological tissue to reduce a muscle stress contraction probability, and also facilitate realizing the continuous conduct of overall pulses including the nanosecond pulse sequence and the millisecond pulse sequence, thereby reducing an idle period, and improving the ablation efficiency.

On the basis of the embodiment above, the inventors of the present application provide the following nine optional implementations of alternately outputting a nanosecond pulse sequence and a millisecond pulse sequence.

Figure 4:
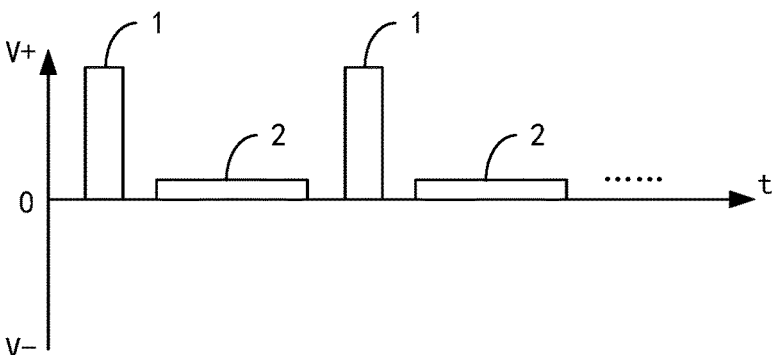
FIG. 4 is a schematic diagram of a pulse waveform of example 1 that is generated by means of a pulse control method provided in an embodiment of the present application.
Figure 8:
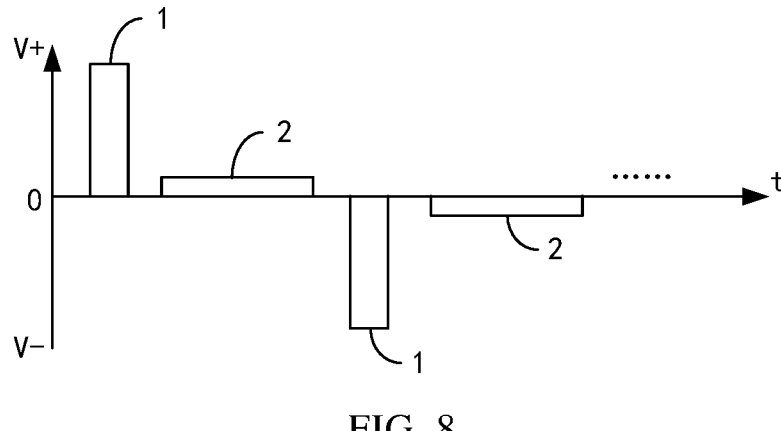
FIG. 8 is a schematic diagram of a pulse waveform of example V that is generated by means of a pulse control method provided in an embodiment of the present application.
Figure 9:
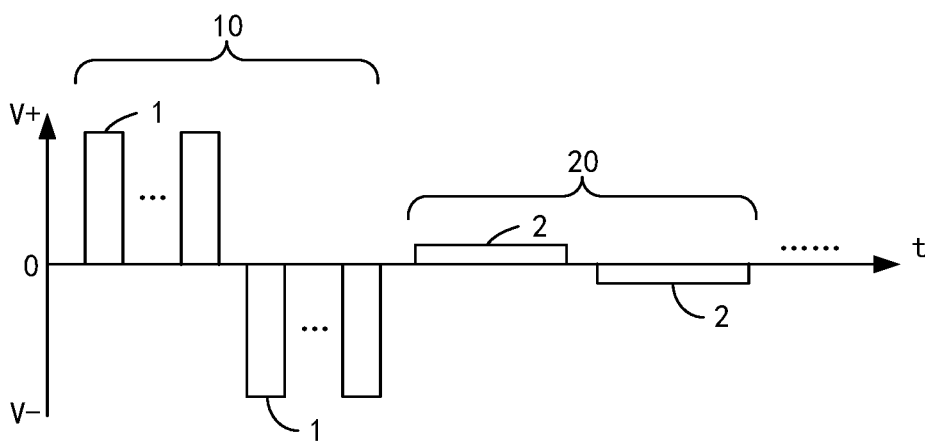
FIG. 9 is a schematic diagram of a pulse waveform of example VI that is generated by means of a pulse control method provided in an embodiment of the present application.

In a first implementation, as shown in FIG. 4 and FIG. 8, each time it is determined that one nanosecond pulse in a nanosecond pulse sequence has been outputted, one millisecond pulse in a millisecond pulse sequence is then outputted.

Optionally, each time determining that the electrode needle 111 has outputted one nanosecond pulse in the nanosecond pulse sequence, the controller 113 in the ablation device 110 provided in the foregoing embodiments then controls the pulse generator 112 to generate one millisecond pulse in the millisecond pulse sequence and output same to the electrode needle 111, such that the electrode needle 111 outputs one millisecond pulse in the millisecond pulse sequence to the target biological tissue.

In the present embodiment, each nanosecond pulse in the nanosecond pulse sequence and each millisecond pulse in the millisecond pulse sequence are alternately generated and outputted in sequence. The high-voltage nanosecond pulse is generated and outputted first, and the low-voltage millisecond pulse is generated and outputted thereafter.

In a second implementation, each time it is determined that one millisecond pulse in a millisecond pulse sequence has been outputted, one nanosecond pulse in a nanosecond pulse sequence is then outputted.

Optionally, each time determining that the electrode needle 111 has outputted one millisecond pulse in the millisecond pulse sequence, the controller 113 in the ablation device 110 provided in the foregoing embodiments then controls the pulse generator 112 to generate one nanosecond pulse in the nanosecond pulse sequence and output same to the electrode needle 111, such that the electrode needle 111 outputs one nanosecond pulse in the nanosecond pulse sequence to the target biological tissue.

In the present embodiment, each nanosecond pulse in the nanosecond pulse sequence and each millisecond pulse in the millisecond pulse sequence are alternately generated and outputted in sequence. The low-voltage millisecond pulse is generated and outputted first, and the high-voltage nanosecond pulse is generated and outputted thereafter.

In a third implementation, as shown in FIG. 5, FIG. 7, FIG. 9, FIG. 11, FIG. 13 and FIG. 14, each time it is determined that at least some nanosecond pulses in a nanosecond pulse sequence have been outputted, at least some millisecond pulses in a millisecond pulse sequence are then outputted.

Optionally, each time determining that the electrode needle 111 has outputted at least some nanosecond pulses in the nanosecond pulse sequence, the controller 113 in the ablation device 110 provided in the foregoing embodiments then controls the pulse generator 112 to generate at least some millisecond pulses in the millisecond pulse sequence and output same to the electrode needle 111, such that the electrode needle 111 outputs the at least some millisecond pulses in the millisecond pulse sequence to the target biological tissue.

In the present embodiment, each nanosecond pulse sub-sequence in the nanosecond pulse sequence and each millisecond pulse sub-sequence in the millisecond pulse sequence are alternately generated and outputted in sequence. The high-voltage nanosecond pulse sub-sequence is generated and outputted first, and the low-voltage millisecond pulse sub-sequence is generated and outputted thereafter.

For example, the nanosecond pulse sequence sequentially includes: a first nanosecond pulse, a second nanosecond pulse, a third nanosecond pulse, a fourth nanosecond pulse, a fifth nanosecond pulse and a sixth nanosecond pulse. The first nanosecond pulse and the second nanosecond pulse form a first nanosecond pulse sub-sequence, the third nanosecond pulse and the fourth nanosecond pulse form a second nanosecond pulse sub-sequence, and the fifth nanosecond pulse and the sixth nanosecond pulse form a third nanosecond pulse sub-sequence.

The millisecond pulse sequence sequentially includes: a first millisecond pulse, a second millisecond pulse, a third millisecond pulse, a fourth millisecond pulse, a fifth millisecond pulse and a sixth millisecond pulse. The first millisecond pulse and the second millisecond pulse form a first millisecond pulse sub-sequence, the third millisecond pulse and the fourth millisecond pulse form a second millisecond pulse sub-sequence, and the fifth millisecond pulse and the sixth millisecond pulse form a third millisecond pulse sub-sequence.

When determining that the electrode needle 111 has outputted the first nanosecond pulse sub-sequence (including the first nanosecond pulse and the second nanosecond pulse), the controller 113 in the ablation device 110 provided in foregoing embodiments then controls the pulse generator 112 to generate the first millisecond pulse sub-sequence (including the first millisecond pulse and the second millisecond pulse) and output same to the electrode needle 111, and so on.

In a fourth implementation, each time it is determined that at least some millisecond pulses in the millisecond pulse sequence have been outputted, at least some nanosecond pulses in the nanosecond pulse sequence are then outputted.

Optionally, each time determining that the electrode needle 111 has outputted at least some millisecond pulses in the millisecond pulse sequence, the controller 113 in the ablation device 110 provided in the foregoing embodiments then controls the pulse generator 112 to generate at least some nanosecond pulses in the nanosecond pulse sequence and output same to the electrode needle 111, and causes the electrode needle 111 to output at least some nanosecond pulses in the nanosecond pulse sequence to the target biological tissue.

In the present embodiment, each nanosecond pulse sub-sequence in the nanosecond pulse sequence and each millisecond pulse sub-sequence in the millisecond pulse sequence are alternately generated and outputted in sequence. The low-voltage millisecond pulse sub-sequence is generated and outputted first, and the high-voltage nanosecond pulse sub-sequence is generated and outputted thereafter.

Figure 10:
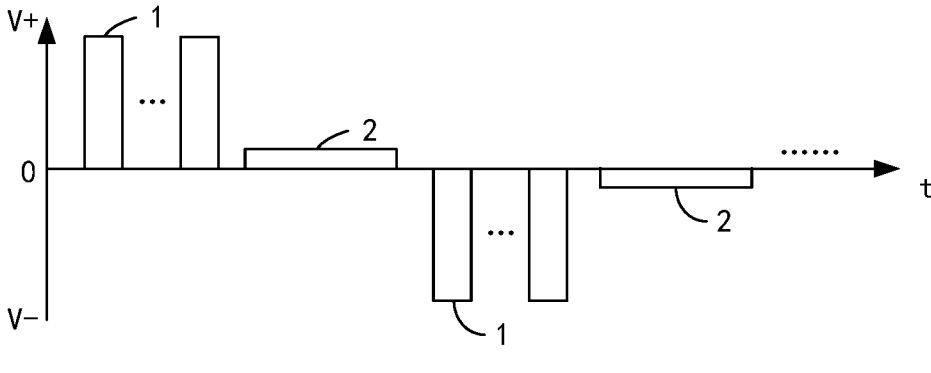
FIG. 10 is a schematic diagram of a pulse waveform of example VII that is generated by means of a pulse control method provided in an embodiment of the present application.
Figure 11:
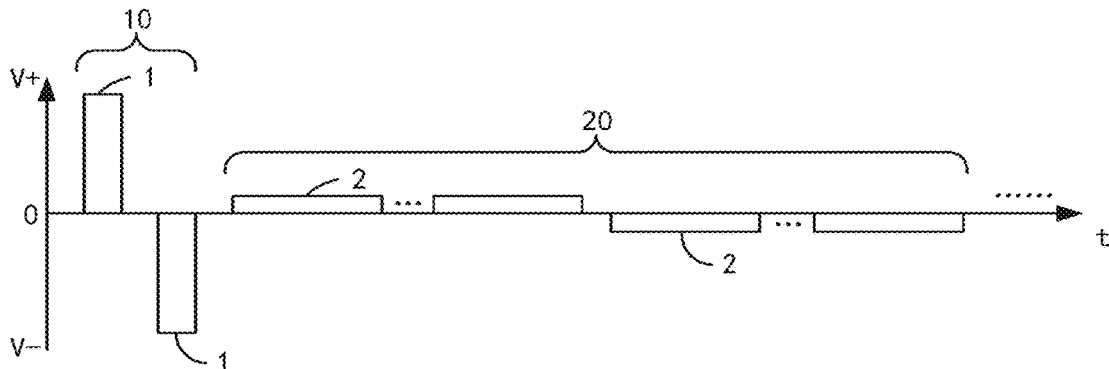
FIG. 11 is a schematic diagram of a pulse waveform of example VIII that is generated by means of a pulse control method provided in an embodiment of the present application.

In a fifth implementation, as shown in FIG. 10, each time it is determined that at least some nanosecond pulses in a nanosecond pulse sequence have been outputted, one millisecond pulse in a millisecond pulse sequence is then outputted.

Optionally, each time determining that the electrode needle 111 has outputted at least some nanosecond pulses in the nanosecond pulse sequence, the controller 113 in the ablation device 110 provided in the foregoing embodiments then controls the pulse generator 112 to generate one millisecond pulse in the millisecond pulse sequence and output same to the electrode needle 111, and causes the electrode needle 111 to output one millisecond pulse in the millisecond pulse sequence to the target biological tissue.

In the present embodiment, each nanosecond pulse sub-sequence in the nanosecond pulse sequence and each millisecond pulse in the millisecond pulse sequence are alternately generated and outputted in sequence. The high-voltage nanosecond pulse sub-sequence is generated and outputted first, and the low-voltage millisecond pulse is generated and outputted thereafter.

Figure 12:
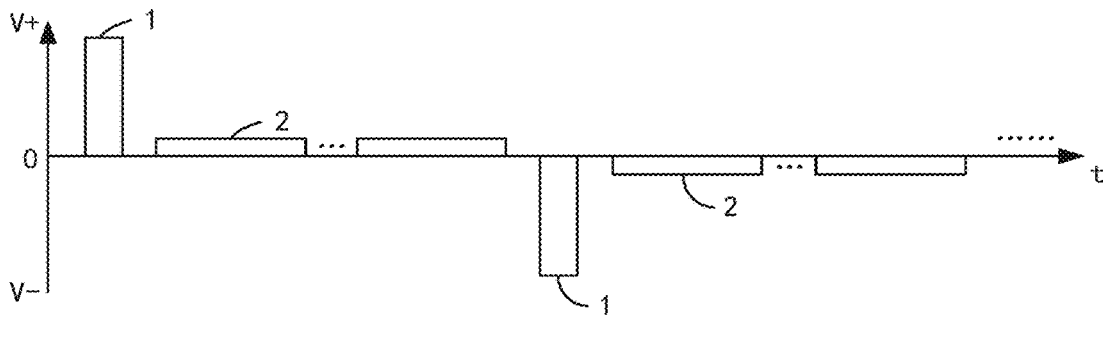
FIG. 12 is a schematic diagram of a pulse waveform of example IX that is generated by means of a pulse control method provided in an embodiment of the present application.
Figure 13:
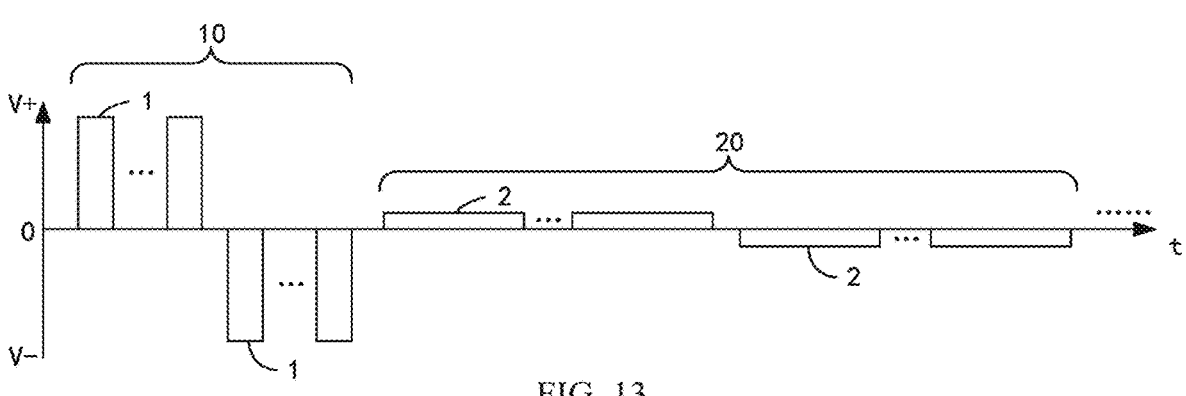
FIG. 13 is a schematic diagram of a pulse waveform of example X that is generated by means of a pulse control method provided in an embodiment of the present application.
Figure 14:
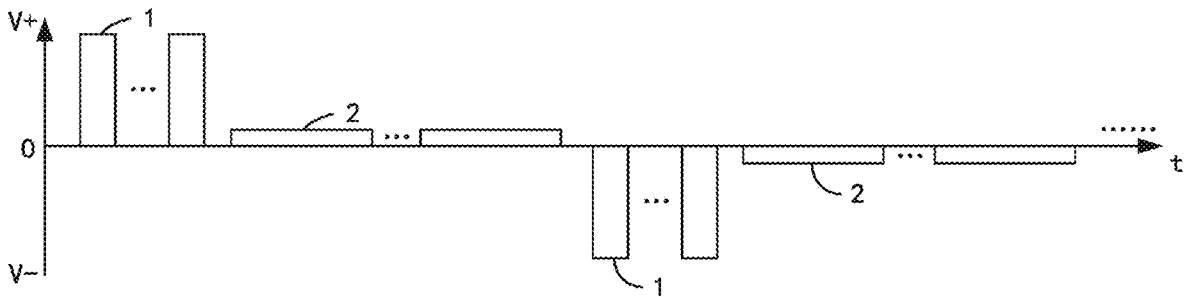
FIG. 14 is a schematic diagram of a pulse waveform of example XI that is generated by means of a pulse control method provided in an embodiment of the present application.

In a sixth implementation, as shown in FIG. 12, each time it is determined that at least some millisecond pulses in a millisecond pulse sequence have been outputted, one nanosecond pulse in a nanosecond pulse sequence is then outputted.

Optionally, each time determining that the electrode needle 111 has outputted at least some millisecond pulses in the millisecond pulse sequence, the controller 113 in the ablation device 110 provided in the foregoing embodiments then controls the pulse generator 112 to generate one nanosecond pulse in the nanosecond pulse sequence and output same to the electrode needle 111, and causes the electrode needle 111 to output one nanosecond pulse in the nanosecond pulse sequence to the target biological tissue.

In the present embodiment, one nanosecond pulse in the nanosecond pulse sequence and each millisecond pulse sub-sequence in the millisecond pulse sequence are alternately generated and outputted in sequence. The low-voltage millisecond pulse sub-sequence is generated and outputted first, and the high-voltage nanosecond pulse is generated and outputted thereafter.

Figure 5:
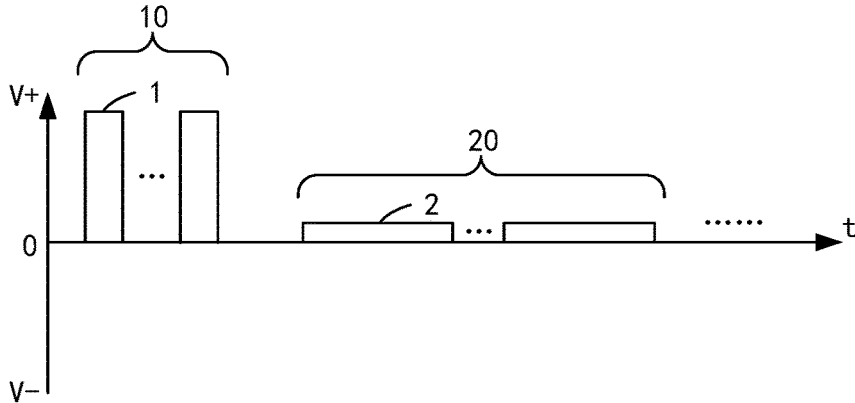
FIG. 5 is a schematic diagram of a pulse waveform of example II that is generated by means of a pulse control method provided in an embodiment of the present application.

In a seventh implementation, as shown in FIG. 4 and FIG. 5, a set interval exists between at least one nanosecond pulse and an adjacent millisecond pulse.

Optionally, the controller 113 in the ablation device 110 provided in the foregoing embodiments controls the pulse generator 112 to generate one nanosecond pulse or one nanosecond pulse sub-sequence in the nanosecond pulse sequence and output same to the electrode needle 111, and after a pause of the set interval, controls the pulse generator 112 to generate one millisecond pulse or one millisecond pulse sub-sequence in the millisecond pulse sequence and output same to the electrode needle 111.

Alternatively, the controller 113 in the ablation device 110 provided in the foregoing embodiments controls the pulse generator 112 to generate one millisecond pulse or one millisecond pulse sub-sequence in the millisecond pulse sequence and output same to the electrode needle 111, and after a pause of the set interval, controls the pulse generator 112 to generate one nanosecond pulse or one nanosecond pulse sub-sequence in the nanosecond pulse sequence and output same to the electrode needle 111.

In the present embodiment, a pause of the set interval may be taken at a change node between a nanosecond pulse and a millisecond pulse, which is conducive to providing a buffer time for cells in the target biological tissue, so as to meet requirements in some treatment scenarios.

Optionally, the set interval is not shorter than 1 nanosecond and not longer than 1 second. In this way, it is conducive to extending effects of an electric pulse action for the cells in the target biological tissue to an extent, and the probability of the cells in the target biological tissue being completely not affected an electric pulse action is reduced, thereby ensuring the ablation effect.

Figure 6:
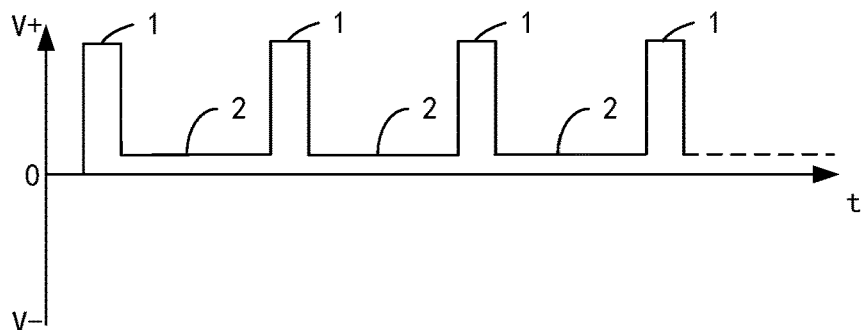
FIG. 6 is a schematic diagram of a pulse waveform of example III that is generated by means of a pulse control method provided in an embodiment of the present application.
Figure 7:
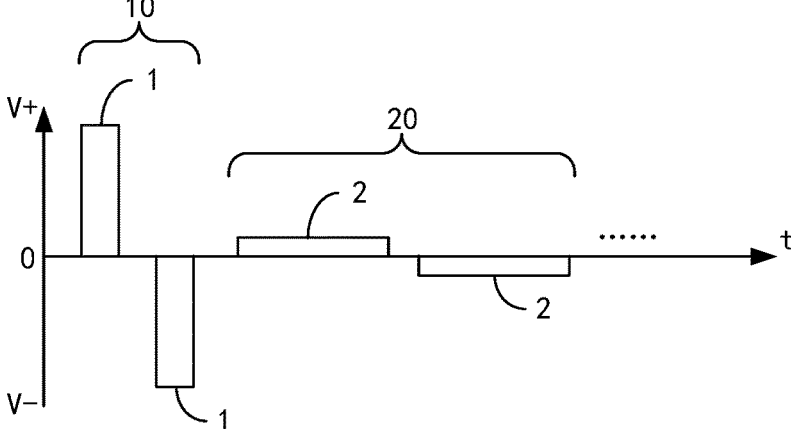
FIG. 7 is a schematic diagram of a pulse waveform of example IV that is generated by means of a pulse control method provided in an embodiment of the present application.

In an eighth implementation, as shown in FIG. 6, a falling edge of at least one nanosecond pulse corresponds to a rising edge of an adjacent millisecond pulse.

Optionally, each time determining that the electrode needle 111 has outputted one nanosecond pulse in a nanosecond pulse sequence or the last nanosecond pulse in one nanosecond pulse sub-sequence, the controller 113 in the ablation device 110 provided in the foregoing embodiments immediately controls the pulse generator 112 to generate one millisecond pulse or one millisecond pulse sub-sequence in a millisecond pulse sequence and output same to the electrode needle 111.

In the present embodiment, conversion between a nanosecond pulse and a millisecond pulse which are adjacent to each other is seamless without a pause interval, thereby facilitating providing a continuous electric pulse action for cells in a target biological tissue and facilitating reduction in a treatment time, and improving the intensity of the electric pulse action.

In a ninth implementation, a rising edge of at least one nanosecond pulse corresponds to a falling edge of an adjacent millisecond pulse.

Optionally, each time determining that the electrode needle 111 has outputted one millisecond pulse in a millisecond pulse sequence or the last millisecond pulse in one millisecond pulse sub-sequence, the controller 113 in the ablation device 110 provided in the foregoing embodiments immediately controls the pulse generator 112 to generate one nanosecond pulse or one nanosecond pulse sub-sequence in a nanosecond pulse sequence and output same to the electrode needle 111.

It should be noted that the alternate outputting manner of the nanosecond pulse sequence and the millisecond pulse sequence is not limited to the implementations provided in the above embodiments.

The inventors of the present application take into consideration that the high-voltage nanosecond pulse sequence can cause irreversible electroporation to occur in cells close to the electrode needle such that the cells enter an apoptosis process, and cause reversible electroporation to occur in cells relatively far from the electrode needle, so as to reduce muscle stress contractions. Therefore, the present application provides the following possible implementations for related parameters or features of a nanosecond pulse sequence.

Optionally, a frequency of the nanosecond pulse sequence is not less than 0.1 Hz and not greater than 10 Hz.

Optionally, the nanosecond pulse sequence includes no less than two nanosecond pulses and no more than 5000 nanosecond pulses.

Optionally, a pulse width of at least one nanosecond pulse in the nanosecond pulse sequence is not less than 10 nanoseconds and not greater than 1000 nanoseconds.

Optionally, an amplitude of at least one nanosecond pulse in the nanosecond pulse sequence is not less than 5 kV and not greater than 100 kV.

Optionally, the nanosecond pulse sequence is a square wave pulse sequence.

Optionally, as shown in FIG. 7 to FIG. 14, the nanosecond pulse sequence is a bipolar pulse sequence.

The inventors of the present application take into consideration that the low-voltage millisecond pulse sequence can conduct electrolysis of cells that are relatively far from the electrode needle and undergo reversible electroporation, such that the cells that are relatively far from the electrode needle can also enter an apoptosis process. Therefore, the present application provides the following possible implementations for related parameters or features of a millisecond pulse sequence.

Optionally, a frequency of the millisecond pulse sequence is not less than 0.1 Hz and not greater than 10 Hz.

Optionally, the millisecond pulse sequence includes no less than 2 millisecond pulses and no more than 5000 millisecond pulses.

Optionally, a pulse width of at least one millisecond pulse in the millisecond pulse sequence is not less than 1 ms and not greater than 1000 ms.

Optionally, an amplitude of at least one millisecond pulse in the millisecond pulse sequence is not less than 5 kV and not greater than 100 kV.

Optionally, the millisecond pulse sequence is a square wave pulse sequence.

Optionally, as shown in FIG. 7 to FIG. 14, the millisecond pulse sequence is a bipolar pulse sequence.

On the basis of the same inventive concept, an embodiment of the present application provides a pulse control apparatus, including, but not limited to: an electric pulse control module.

The electric pulse control module is configured to output a nanosecond pulse sequence and a millisecond pulse sequence to a target biological tissue. An amplitude of the nanosecond pulse sequence is greater than a threshold voltage, and an amplitude of the millisecond pulse sequence is less than a threshold voltage.

In the present embodiment, the nanosecond pulse sequence having the amplitude greater than the threshold voltage cooperates with the millisecond pulse sequence having the amplitude less than the threshold voltage, such that the pulse control apparatus can enlarge the effective ablation range, and achieve more thorough ablation; the pulse control apparatus can also effectively reduce the muscle contraction amplitude or the muscle contraction probability, or even avoid muscle contractions, thereby improving the treatment experience of a patient; and the pulse control apparatus can reduce the use of anesthetics or even not need same, thereby effectively reducing treatment costs and reducing side effects.

Specifically, the high-voltage nanosecond pulse sequence can cause irreversible electroporation to occur in cells close to the electrode needle 111 such that the cells enter an apoptosis process, and cause reversible electroporation to occur in cells relatively far from the electrode needle 111. The low-voltage millisecond pulse sequence can conduct electrolysis of the cells relatively far from the electrode needle 111 in which reversible electroporation occurs (water and an electrolyte are present in the cells, and under a certain electrolysis condition, the electrolyte may be bound with hydroxide ions generated by water electrolysis, so as to reduce the concentration of the electrolyte, such that osmotic pressure equilibrium, acid-base equilibrium, water equilibrium, etc. of the cells may be broken, thereby destroying cell activity), and thus the cells relatively far from the electrode needle 111 may also enter the apoptosis process. Therefore, compared with the existing electroablation solution, a larger ablation treatment range and more thorough ablation are achieved by means of the technical solution provided in the embodiments of the present application.

Moreover, the high-voltage nanosecond pulse sequence facilitates reduction in muscle stress contractions due to parameter characteristics thereof, and the low-voltage millisecond pulse sequence also does not cause any muscle stress contraction due to a relatively low voltage used thereby. Therefore, by means of the technical solution provided in the embodiments of the present application, muscle contractions of a patient during treatment can be greatly relieved and even avoided, thereby improving the treatment experience of the patient.

In some possible exemplary embodiments, the electric pulse control module is configured to alternatively output a nanosecond pulse sequence and a millisecond pulse sequence to a target biological tissue.

Optionally, the electric pulse control module is configured to output one millisecond pulse in the millisecond pulse sequence each time determining that one nanosecond pulse in the nanosecond pulse sequence has been outputted.

Optionally, the electric pulse control module is configured to output one nanosecond pulse in the nanosecond pulse sequence each time determining that one millisecond pulse in the millisecond pulse sequence has been outputted.

Optionally, the electric pulse control module is used for outputting at least some millisecond pulses in the millisecond pulse sequence each time determining that at least some nanosecond pulses in the nanosecond pulse sequence have been outputted.

Optionally, the electric pulse control module is used for outputting at least some nanosecond pulses in the nanosecond pulse sequence each time determining that at least some millisecond pulses in the millisecond pulse sequence have been outputted.

Optionally, the electric pulse control module is used for outputting one millisecond pulse in the millisecond pulse sequence each time determining that at least some nanosecond pulses in the nanosecond pulse sequence have been outputted.

Optionally, the electric pulse control module is used for outputting one nanosecond pulse in the nanosecond pulse sequence each time determining that at least some millisecond pulses in the millisecond pulse sequence have been outputted.

On the basis of the same inventive concept, an embodiment of the present application provides a computer-readable storage medium, the computer-readable storage medium having a computer program stored thereon, and the computer program, when executed by a processor, implementing any pulse control method provided in the embodiments of the present application.

The embodiments of the present application provide a computer-readable storage medium, which is suitable for various optional implementations of any one of the above pulse control methods. The details are not repeated here.

It should be understood by the skilled in the art that the computer-readable storage medium provided in the present embodiment may be any available medium that can be accessed by an electronic device and includes a volatile medium, a non-volatile medium, and a removable medium or a non-removable medium. The computer-readable storage medium includes, but not limited to any types of disks (including a floppy disc, a hard disc, a compact disc, a CD-ROM and a magneto-optical disc), a ROM, a RAM, an erasable programmable read-only memory (EPROM), an electrically erasable programmable read only memory (EE-PROM), a flash memory, a magnetic card or a optical card. That is to say, the computer-readable storage medium includes any medium by means of which a device (e.g., a computer) stores information in a readable manner or transmits information.

Figure 3:
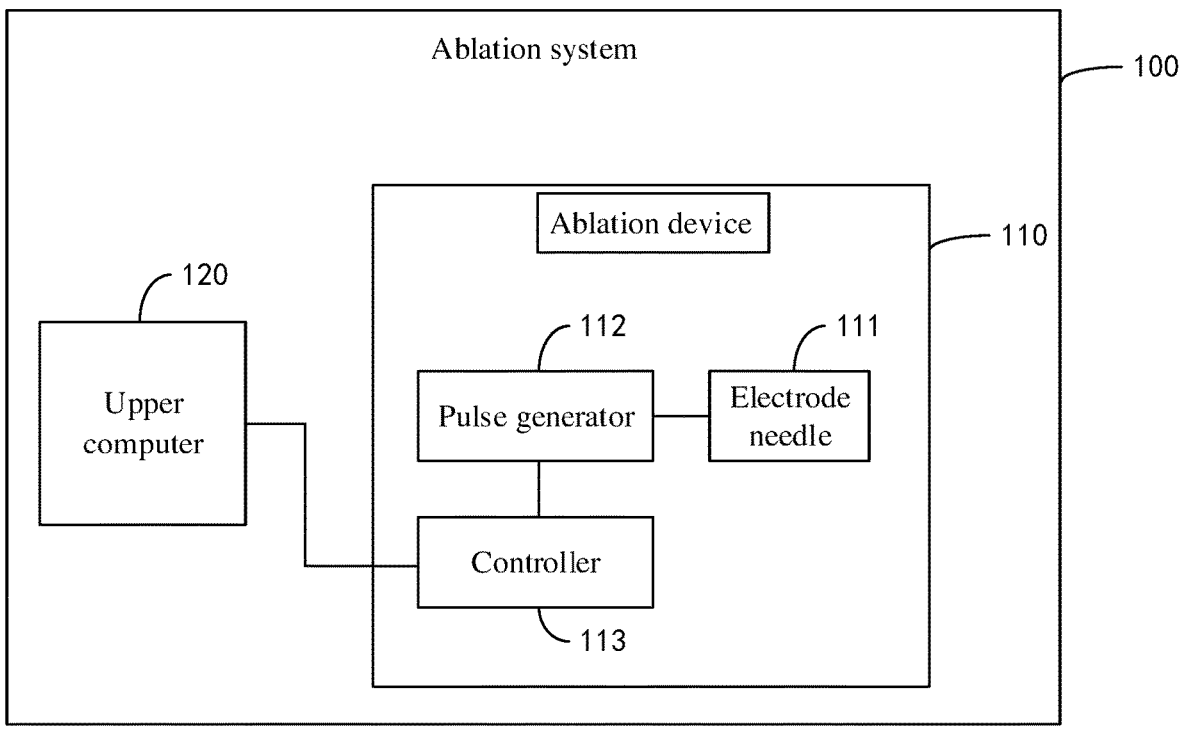
FIG. 3 is a schematic diagram of a framework of the structure of an ablation device provided in an embodiment of the present application.

On the basis of the same inventive concept, an embodiment of the present application provides an ablation system 100. FIG. 3 shows a schematic diagram of a framework of the system, including, but not limited to: any ablation device 110 according to the foregoing embodiments, and an upper computer 120. The upper computer 120 is communicatively connected with a controller 113 in the ablation device 110.

In the present embodiment, the upper computer 120 can realize a program update or data backup of the ablation device 110, and can also realize remote control over the ablation device 110, so as to facilitate function extension of the ablation device 110.

Optionally, the upper computer 120 is communicatively connected with the controller 113 in the ablation device 110 by means of wireless fidelity (WiFi, which is also referred to as a mobile hotspot).

Optionally, the upper computer 120 is communicatively connected with the controller 113 in the ablation device 110 by means of cloud.

Several groups of experimental examples and comparative examples will be given below to demonstrate the effect of a cooperative action of the high-voltage nanosecond pulse sequence and the low-voltage millisecond pulse sequence in the embodiments of the present application.

In the following experimental examples and comparative examples, experimental subjects are all New Zealand white rabbits (female, 6 months old, and 2.5 kg plus or minus 0.2 kg in weight). The New Zealand white rabbits are provided by Laboratory Animal Centre of Chongqing Medical University, and are bred in a clean and thermostatic animal breeding laboratory.

In the experimental examples and comparative examples, the ablation device 110 developed independently by the company is used, including an electrode needle 111, a pulse generator 112 and a controller 113. A pulse that the pulse generator 112 of the ablation device 110 can output include parameters of 10 ns to 100 ms, an adjustable amplitude of 0 kV to 200 kV, and a frequency of 0.1 kHz to 1 kHz. The electrode needle can be made of medical stainless steel by the company itself. The electrode needle has a diameter of 1 mm and an exposure length of 8 mm, and electrode spacings are uniformly fixed to 10 mm using a separator made by the company itself.

In experimental example 1, a cooperative action of the high-voltage nanosecond pulse sequence and the low-voltage millisecond pulse sequence is used; see table 1 for related data.

TABLE 1

| Experimental example 1 | Nanosecond pulse | Millisecond pulse |
|---|---|---|
| Pulse width | 300 nanoseconds (ns) | 1 millisecond (ms) |
| Amplitude | 10 kilovolts (kV) | 50 volts (V) |
| Count | 250 | 250 |
| Electrode needle spacing | 100 millimeters (mm) | |
| Muscle contraction manifestation | No significant muscle contraction | |
| Ablation area | 95 square millimeters (mm$^2$) | |
| Length and width of ablation region | Maximum length: 17 millimeters (mm); maximum width: 10 mm | |

In experimental example 2, a cooperative action of the high-voltage nanosecond pulse sequence and the low-voltage millisecond pulse sequence is used; see table 2 for related data.

TABLE 2

| Experimental example 2 | Nanosecond pulse | Millisecond pulse |
|---|---|---|
| Pulse width | 300 ns | 5 ms |
| Amplitude | 10 kV | 50 V |
| Count | 250 | 250 |
| Electrode needle spacing | 10 mm | |
| Muscle contraction manifestation | No significant muscle contraction | |
| Ablation area | 108 mm$^2$ | |
| Length and width of ablation region | Maximum length: 17 mm; maximum width: 11 mm | |

In experimental example 3, a cooperative action of the high-voltage nanosecond pulse sequence and the low-voltage millisecond pulse sequence is used; see table 3 for related data.

TABLE 3

| Experimental example 3 | Nanosecond pulse | Millisecond pulse |
|---|---|---|
| Pulse width | 300 ns | 10 ms |
| Amplitude | 10 kV | 50 V |
| Count | 250 | 250 |
| Electrode needle spacing | 10 mm | |
| Muscle contraction manifestation | No significant muscle contraction | |
| Ablation area | 128 mm$^2$ | |
| Length and width of ablation region | Maximum length: 18 mm; maximum width: 11.8 mm | |

In comparative example 1, a high-voltage microsecond pulse sequence is used; see table 4 for related data.

TABLE 4

| Comparative example 1 | Microsecond pulse |
|---|---|
| Pulse width | 100 microseconds (μs) |
| Amplitude | 1.5 kV |
| Count | 100 |
| Electrode needle spacing | 10 mm |
| Muscle contraction manifestation | Intense muscle contraction, with the contraction intensity of 4 grams (g) |
| Ablation area | 110 mm$^2$ |
| Length and width of ablation region | Maximum length: 17 mm; maximum width: 11.2 mm |

It can be seen, from the related data of experimental examples 1 to 3 and comparative example 1, that by means of the cooperative action of the high-voltage nanosecond pulse sequence and the low-voltage millisecond pulse sequence, a larger effective ablation range and more thorough ablation can be achieved, and muscle contractions can also be effectively suppressed.

By means of the embodiments of the present application, at least the following beneficial effects can be realized.

1. A nanosecond pulse sequence having an amplitude greater than a threshold voltage cooperates with a millisecond pulse sequence having an amplitude less than the threshold voltage, such that the effective ablation range can be enlarged, and the ablation can be more thorough; the muscle contraction amplitude or the muscle contraction probability can be effectively reduced, or muscle contractions can even be avoided, thereby improving the treatment experience of a patient; and the use of anesthetics can be reduced or even not needed, thereby effectively reducing treatment costs and reducing side effects.

2. The nanosecond pulse sequence and the millisecond pulse sequence are alternately outputted to a target biological tissue, so as to facilitate controlling the length of the high-voltage nanosecond pulse sequence, that is, controlling an action duration of each high-voltage nanosecond pulse sequence on the target biological tissue to reduce a muscle stress contraction probability, and also facilitate realizing the continuous conduct of overall pulses including the nanosecond pulse sequence and the millisecond pulse sequence, thereby reducing an idle period, and improving the ablation efficiency.

3. A pause of a set interval may be taken at a change node between a nanosecond pulse and a millisecond pulse, which is conducive to providing a buffer time for cells in the target biological tissue, so as to meet requirements in some treatment scenarios.

4. Conversion between a nanosecond pulse and a millisecond pulse which are adjacent to each other is seamless without a pause interval, thereby facilitating providing a continuous electric pulse action for the cells in the target biological tissue and facilitating reduction in a treatment time, and improving the intensity of the electric pulse action.

It should be understood by the skilled in the art that various operations, methods, steps in a process, measures and solutions that have been discussed in the present application may be alternated, modified, combined or deleted. Furthermore, other steps, measures and solutions having the various operations, methods, and steps in the process that have been discussed in the present application may also be alternated, modified, re-arranged, decomposed, combined or deleted. Furthermore, steps, measures and solutions in the prior art that have the various operations, methods, and steps in the process that have been discussed in the present application may also be alternated, modified, re-arranged, decomposed, combined or deleted.

In the description of the present application, it should be understood that orientation or position relationships indicated by terms such as "center", "up", "down", "front", "rear", "left", "right", "vertical", "horizontal", "top", "bottom", "inside", and "outside" are based on orientation or position relationships shown in the drawings and are merely for ease of description of the present application and simplification of the description, rather than indicating or implying that the apparatuses or elements referred to must have a specific orientation or be constructed and operated in a specific orientation, and therefore cannot be construed as limiting the present application.

The terms "first" and "second" are used for descriptive purposes only, and cannot be construed as indicating or implying relative importance or implicitly indicating the number of technical features indicated. Thus, the features defined with "first" and "second" may explicitly or implicitly include one or more features. In the description of the present application, unless otherwise specified, "a plurality of" means two or more.

In the description of the present application, it should be noted that, unless otherwise explicitly specified and defined, the terms "mounting", "connecting" and "connection" should be understood in a broad sense, for example, they may be a fixed connection, a detachable connection, or an integrated connection; and can be directly connected, or indirectly connected by means of an intermediate medium, or communication between interiors of two elements. For those of ordinary skill in the art, the specific meaning of the terms mentioned above in the present application can be construed according to specific circumstances.

In the description of the present specification, the specific features, structures, materials or characteristics may be combined in a suitable manner in any one or more embodiments or examples.

It should be understood that although the steps in the flowcharts in the drawings are displayed in succession as indicated by arrows, these steps are not necessarily executed in succession in the order indicated by the arrows. Unless explicitly specified herein, the execution of these steps is not limited to a strict order, instead, the steps can be executed in another order. In addition, at least some steps in the flowcharts in the drawings may comprise multiple sub-steps or multiple stages. These sub-steps or stages are not necessarily executed or completed at the same moment, but may be executed at different times, and the order of execution thereof is also not necessarily in succession, but may be executed in turn or alternately with at least some other steps or sub-steps or stages of other steps.

The above describes some embodiments of the present application, and it should be noted that for those of ordinary skill in the art, several improvements and modifications can also be made without departing from the principle of the present application, and these improvements and modifications are also considered to be within the scope of protection of the present application.

What is claimed is:

1. A pulse control method, comprising:
controlling a pulse generator to output a nanosecond pulse sequence, and
controlling the pulse generator to output a millisecond pulse sequence,
wherein an amplitude of the nanosecond pulse sequence is greater than a preset first threshold voltage, and an amplitude of the millisecond pulse sequence is less than a preset second threshold voltage, and
wherein the nanosecond pulse sequence causes irreversible electroporation to occur in cells close to an electrode needle such that the cells enter an apoptosis process, and causes reversible electroporation to occur in cells relatively far from the electrode needle;
wherein the millisecond pulse sequence causes intracellular electrolysis of the cells relatively far from the electrode needle in which reversible electroporation occurs, such that the cells relatively far from the electrode needle also enter the apoptosis process.

2. The pulse control method according to claim 1, wherein controlling the pulse generator to output the nanosecond pulse sequence and controlling the pulse generator to output the millisecond pulse sequence comprises:
alternatively outputting the nanosecond pulse sequence and the millisecond pulse sequence.

3. The pulse control method according to claim 2, wherein alternatively outputting the nanosecond pulse sequence and the millisecond pulse sequence comprises:
each time it is determined that one nanosecond pulse in the nanosecond pulse sequence has been outputted, outputting one millisecond pulse in the millisecond pulse sequence; and/or
each time it is determined that one millisecond pulse in the millisecond pulse sequence has been outputted, outputting one nanosecond pulse in the nanosecond pulse sequence.

4. The pulse control method according to claim 2, wherein alternatively outputting the nanosecond pulse sequence and the millisecond pulse sequence comprises:
each time it is determined that at least some nanosecond pulses in the nanosecond pulse sequence have been outputted, outputting at least some millisecond pulses in the millisecond pulse sequence; and/or
each time it is determined that at least some millisecond pulses in the millisecond pulse sequence have been outputted, outputting at least some nanosecond pulses in the nanosecond pulse sequence.

5. The pulse control method according to claim 2, wherein alternatively outputting the nanosecond pulse sequence and the millisecond pulse sequence comprises:
each time it is determined that at least some nanosecond pulses in the nanosecond pulse sequence have been outputted, outputting one millisecond pulse in the millisecond pulse sequence;
and/or each time it is determined that at least some millisecond pulses in the millisecond pulse sequence have been outputted, outputting one nanosecond pulse in the nanosecond pulse sequence.

6. The pulse control method according to claim 3, wherein a set interval exists between at least one nanosecond pulse in the nanosecond pulse sequence and an adjacent millisecond pulse in the millisecond pulse sequence.

7. The pulse control method according to claim 6, wherein the set interval is not shorter than 1 nanosecond and not longer than 1 second.

8. The pulse control method according to claim 3, wherein a falling edge of at least one nanosecond pulse in the nanosecond pulse sequence corresponds to a rising edge of an adjacent millisecond pulse in the millisecond pulse sequence; and/or a rising edge of at least one nanosecond pulse in the nanosecond pulse sequence corresponds to a falling edge of an adjacent millisecond pulse in the millisecond pulse sequence.

9. The pulse control method according to claim 1, wherein a set interval exists between an ending time of at least one nanosecond pulse in the nanosecond pulse sequence and a starting time of a following adjacent millisecond pulse in the millisecond pulse sequence, and the set interval is not longer than 1 second.

10. The pulse control method according to claim 1, wherein the nanosecond pulse sequence includes one or more of the following features:

a frequency of the nanosecond pulse sequence being not less than 0.1 Hz and not greater than 10 Hz;

the nanosecond pulse sequence comprising no less than 2 nanosecond pulses and no more than 5000 nanosecond pulses;

a pulse width of at least one nanosecond pulse in the nanosecond pulse sequence being not less than 10 nanoseconds and not greater than 1000 nanoseconds;

an amplitude of at least one nanosecond pulse in the nanosecond pulse sequence being not less than 5 kV and not greater than 100 kV;

the nanosecond pulse sequence being a square wave pulse sequence; and the nanosecond pulse sequence being a bipolar pulse sequence.

11. The pulse control method according to claim 1, wherein the millisecond pulse sequence includes one or more of the following features:

a frequency of the millisecond pulse sequence being not less than 0.1 Hz and not greater than 10 Hz;

the millisecond pulse sequence comprising no less than 2 millisecond pulses and no more than 5000 millisecond pulses;

a pulse width of at least one millisecond pulse in the millisecond pulse sequence being not less than 1 ms and not greater than 1000 ms;

an amplitude of at least one millisecond pulse in the millisecond pulse sequence being not less than 5 V and not greater than 100 V;

the millisecond pulse sequence being a square wave pulse sequence; and the millisecond pulse sequence being a bipolar pulse sequence.

12. A pulse control apparatus, comprising:

an electric pulse control module configured to control a pulse generator to output a nanosecond pulse sequence and control the pulse generator to output a millisecond pulse sequence; and control an amplitude of the nanosecond pulse sequence to be greater than a preset first threshold voltage and control an amplitude of the millisecond pulse sequence to be less than a preset second threshold voltage, and wherein the nanosecond pulse sequence causes irreversible electroporation to occur in cells close to an electrode needle such that the cells enter an apoptosis process, and causes reversible electroporation to occur in cells relatively far from the electrode needle;

wherein the millisecond pulse sequence causes intracellular electrolysis of the cells relatively far from the electrode needle in which reversible electroporation occurs, such that the cells relatively far from the electrode needle also enter the apoptosis process.

13. An ablation device, comprising:

an electrode needle configured to contact a target object and output an electric pulse to the target object, the electric pulse comprising a nanosecond pulse sequence and a millisecond pulse sequence;

a pulse generator electrically connected to the electrode needle and configured to generate the electric pulse and conduct the electric pulse to the electrode needle; and a controller communicatively connected with the pulse generator and configured to perform a pulse control method comprising:

controlling the pulse generator to output the nanosecond pulse sequence, and controlling the pulse generator to output the millisecond pulse sequence, wherein an amplitude of the nanosecond pulse sequence is greater than a preset first threshold voltage, and an amplitude of the millisecond pulse sequence is less than a preset second threshold voltage, and wherein the nanosecond pulse sequence causes irreversible electroporation to occur in cells close to the electrode needle such that the cells enter an apoptosis process, and causes reversible electroporation to occur in cells relatively far from the electrode needle;

wherein the millisecond pulse sequence causes intracellular electrolysis of the cells relatively far from the electrode needle in which reversible electroporation occurs, such that the cells relatively far from the electrode needle also enter the apoptosis process.

14. The ablation device according to claim 13, wherein the pulse generator comprises:

a first sub-generator electrically connected to the electrode needle, communicatively connected with the controller and configured to generate the nanosecond pulse sequence; and a second sub-generator electrically connected to the electrode needle, communicatively connected with the controller and configured to generate the millisecond pulse sequence.

15. An ablation system comprising the ablation device according to claim 13 and an upper computer, the upper computer being communicatively connected with the controller in the ablation device.

16. A non-transitory computer-readable storage medium having a computer program stored therein, wherein the computer program, when executed by a processor, implements the pulse control method according to claim 1.

17. The method according to claim 1, wherein, controlling the pulse generator to output the nanosecond pulse sequence, and controlling the pulse generator to output the millisecond pulse sequence, comprises:

controlling the pulse generator to first output the nanosecond pulse sequence to induce occurrence of reversible cell electropores in the cells relatively far from the electrode needle, and then during existence of at least some of the reversible cell electropores, to output the millisecond pulse sequence.

* * * * *